(12) United States Patent
Nakahata et al.

(10) Patent No.: US 9,404,082 B2
(45) Date of Patent: Aug. 2, 2016

(54) METHOD FOR PRODUCTION OF EOSINOPHIL FROM PLURIPOTENT STEM CELL

(75) Inventors: Tatsutoshi Nakahata, Kyoto (JP); Kohichiro Tsuji, Tokyo (JP); Feng Ma, Tokyo (JP); Hirohisa Saito, Tokyo (JP); Kenji Matsumoto, Tokyo (JP)

(73) Assignee: KYOTO UNIVERSITY, Kyoto-shi, Kyoto (JP)

( * ) Notice: Subject to any disclaimer, the term of this patent is extended or adjusted under 35 U.S.C. 154(b) by 196 days.

(21) Appl. No.: 13/990,991

(22) PCT Filed: Dec. 2, 2011

(86) PCT No.: PCT/JP2011/077955
§ 371 (c)(1),
(2), (4) Date: Jun. 12, 2013

(87) PCT Pub. No.: WO2012/074106
PCT Pub. Date: Jun. 7, 2012

(65) Prior Publication Data
US 2015/0104820 A1 Apr. 16, 2015

Related U.S. Application Data

(60) Provisional application No. 61/419,496, filed on Dec. 3, 2010.

(51) Int. Cl.
| | |
|---|---|
| C12N 5/00 | (2006.01) |
| C12N 5/08 | (2006.01) |
| C12Q 1/02 | (2006.01) |
| C12N 5/0787 | (2010.01) |
| C12N 5/074 | (2010.01) |
| G01N 33/50 | (2006.01) |

(52) U.S. Cl.
CPC ............ *C12N 5/0642* (2013.01); *G01N 33/505* (2013.01); *G01N 33/5029* (2013.01); *C12N 5/0696* (2013.01); *C12N 2501/125* (2013.01); *C12N 2501/145* (2013.01); *C12N 2501/165* (2013.01); *C12N 2501/20* (2013.01); *C12N 2501/22* (2013.01); *C12N 2501/2303* (2013.01); *C12N 2501/2305* (2013.01); *C12N 2501/2306* (2013.01); *C12N 2501/26* (2013.01); *C12N 2502/02* (2013.01); *C12N 2506/02* (2013.01); *C12N 2506/45* (2013.01); *G01N 33/5047* (2013.01); *G01N 2500/04* (2013.01); *G01N 2500/10* (2013.01)

(58) Field of Classification Search
CPC ............... C12N 5/0642; C12N 5/0696; C12N 2502/02; C12N 2501/2303; C12N 2501/2306; C12N 2506/45; G01N 33/5029; G01N 33/5047; G01N 2500/10
USPC .................... 435/29, 372, 377, 384
See application file for complete search history.

(56) References Cited

U.S. PATENT DOCUMENTS

| 8,048,999 B2 | 11/2011 | Yamanaka et al. |
| 8,093,049 B2 | 1/2012 | Tseng et al. |
| 2012/0028288 A1 | 2/2012 | Nitta |

FOREIGN PATENT DOCUMENTS

| WO | WO 99/03980 A1 | 1/1999 |
| WO | WO 2007/066684 A1 | 6/2007 |
| WO | WO 2007/069666 A1 | 6/2007 |
| WO | WO 2009/120891 A2 | 10/2009 |

OTHER PUBLICATIONS

Allegrucci et al., 2006, Human Reproduction Update, vol. Advance Access published on Aug. 26, 2006, p. 1-18.*
Sato et al., 2003, Developmental Biology, vol. 260, p. 404-413.*
Abeyta et al., 2004, Human Molecular Genetics, vol. 13, No. 6, p. 601-608.*
Bellin et al., 2012, Nature reviews/Molecular Cell Biology, vol. 13, p. 713-726.*
Burridge et al., 2011, PLoS ONE, vol. 6, No. 4, e18293, p. 1-16.*
International Search Report for International Application No. PCT/JP2011/077955, mailed on Feb. 21, 2012.
Takahashi et al., "Induction of Pluripotent Stem Cells from Mouse Embryonic and Adult Fibroblast Cultures by Defined Factors," *Cell*, vol. 126, pp. 663-676 (Aug. 25, 2006).
Takahashi et al., "Induction of Pluripotent Stem Cells from Adult Human Fibroblasts by Defined Factors," *Cell*, vol. 131, pp. 861-872 (Nov. 30, 2007).
Tsuru et al., "ES saibo Kara Kosankyu eno Bunka" (Differentiation from ES cells into eosinophils), *Inflammation & Immunology*, vol. 14(1), pp. 3-9 (2006).
Ueda et al., "Expansion of human NOD/SCID-repopulating cells by stem cell factor, Flk2/Flt3 ligand, thrombopoietin, IL-6, and soluble IL-6 receptor," *The Journal of Clinical Investigation*, vol. 105(7), pp. 1013-1021 (Apr. 2000).
Extended European Search Report for European Patent Application No. 11845927.0, dated Sep. 3, 2015.

(Continued)

*Primary Examiner* — Shin Lin Chen
(74) *Attorney, Agent, or Firm* — Knobbe, Martens, Olson & Bear, LLP

(57) ABSTRACT

The present invention relates to a method for producing human eosinophils from human pluripotent stem cells. More specifically, the present invention provides a method for producing human eosinophils from human pluripotent stem cells, which method comprises the steps of: (1) co-culturing, in the presence of VEGF, human pluripotent stem cells with cells separated from the AGM region of a mammalian fetus; (2) performing suspension culture using a medium comprising IL-3, IL-6, Flt3 ligand, SCF, TPO and serum; (3) performing suspension culture using a medium comprising IL-3, SCF, GM-CSF and serum; and, optionally, (4) performing suspension culture using a medium comprising IL-3, IL-5 and serum.

7 Claims, 4 Drawing Sheets

(56) References Cited

OTHER PUBLICATIONS

Database Biosis [Online], "Differentiation of Mature Eosinophils From Human Embryonic and Induced Pluripotent Stem Cells", XP002743160, Database accession No. PREV201100424139.

Ma et al., "Generation of Mature Eosinophils from Human Embryonic and Induced Pluripotent Stem Cells," *Experimental Hematology*, vol. 38(Suppl 1), pp. S1-S136 (2010) (Abstract).

* cited by examiner

METHOD FOR PRODUCTION OF EOSINOPHIL FROM PLURIPOTENT STEM CELL

CROSS-REFERENCE TO RELATED APPLICATIONS

This application is the U.S. National Phase under 35 U.S.C. §371 of International Application PCT/JP2011/077955, filed Dec. 2, 2011, which was published in a non-English language, which claims priority to U.S. Provisional Application No. 61/419,496, filed Dec. 3, 2010.

TECHNICAL FIELD

The present invention relates to a method for efficiently producing human eosinophils from human pluripotent stem cells. More specifically, the present invention relates to a method for producing human eosinophils from human pluripotent stem cells, which method comprises the steps of: (1) co-culturing, in the presence of VEGF, human pluripotent stem cells with cells separated from the AGM region of a mammalian fetus; (2) performing culture using a medium comprising IL-3, IL-6, Flt3 ligand, SCF, TPO and serum; (3) performing culture using a medium comprising IL-3, SCF, GM-CSF and serum; and, optionally, (4) performing culture using a medium comprising IL-3, IL-5 and serum.

BACKGROUND ART

An eosinophil is a granulocyte derived from bone marrow, and recruited to an inflammatory site in either natural immunity or acquired immunity. Such a recruited eosinophil is largely involved in diseases such as allergic diseases and asthma. It is said that not less than 20% of the population has abnormalities in allergic reactions, which are primary causes of asthma, pollinosis, rhinitis and dermatitis, and this has become a social problem.

It is now demanded to use eosinophils for development and evaluation of therapeutic agents for allergic diseases.

In recent years, induced pluripotent stem cells (iPS cells) of mouse and human have been established in succession by introduction of the Oct3/4, Sox2, Klf4 and c-Myc genes into fibroblasts followed by their forced expression (Patent Document 1, Non-patent Documents 1 and 2). A method for obtaining mature human eosinophils by efficient differentiation induction from these iPS cells or pluripotent stem cells such as embryonic stem cells is demanded.

PRIOR ART DOCUMENTS

Patent Document

Patent Document 1: WO 2007/069666 A1

Non-Patent Documents

Non-patent Document 1: Takahashi, K. and Yamanaka, S., Cell, 126: 663-676 (2006)
Non-patent Document 2: Takahashi, K. et al., Cell, 131: 861-872 (2007)

SUMMARY OF THE INVENTION

The present invention aims to efficiently produce eosinophils from pluripotent stem cells. Therefore, an object of the present invention is to provide culture conditions under which differentiation from human pluripotent stem cells, especially human induced pluripotent stem cells, into eosinophils is induced.

In order to solve the above object, the present inventors first co-cultured established induced pluripotent stem cells with cells separated from the AGM region of a mouse fetus, and the obtained cells were then cultured in media comprising appropriate cytokines while the media were replaced in a stepwise manner. By this, differentiation induction to mature eosinophils was successfully carried out, thereby the present invention was completed.

[1] A method for producing human eosinophils from human pluripotent stem cells, said method comprising the steps of:
(1) co-culturing, in the presence of VEGF, human pluripotent stem cells with cells separated from the AGM region of a mammalian fetus;
(2) performing suspension culture of the cells obtained in Step (1) using a medium comprising IL-3, IL-6, Flt3 ligand, SCF, TPO and serum;
(3) performing suspension culture of the cells obtained in Step (2) using a medium comprising IL-3, SCF, GM-CSF and serum; and, optionally,
(4) performing suspension culture of the cells obtained in Step (3) using a medium comprising IL-3, IL-5 and serum.
[2] The method according to [1], wherein said cells separated from the AGM region of a mammalian fetus are AGMS-3.
[3] The method according to [1], wherein said human pluripotent stem cells are human induced pluripotent stem cells.
[4] The method according to [1], wherein each of Step (2), Step (3) and Step (4) is carried out for 7 days.
[5] The method according to [1], wherein the concentration of serum is 10% in Step (2), Step (3) and Step (4).
[6] The method according to [1], wherein the produced human eosinophils are eosinophils that migrate in response to stimulation by a cytokine(s).
[7] The method according to [6], wherein said cytokine(s) is/are IL-5, Eotaxin and/or fMLP.
[8] A method for screening a therapeutic agent for bronchial asthma, allergic disease and/or atopic dermatitis, said method comprising the steps of: producing human eosinophils from human induced pluripotent stem cells by the method according to claim 1, and bringing the obtained human eosinophils into contact with test substances to select a test substance that reduces the migratory capacity of said eosinophils.
[9] The screening method according to [8], wherein said human induced pluripotent stem cells are induced pluripotent stem cells produced from somatic cells of a subject suffering from bronchial asthma, allergic disease and/or atopic dermatitis.

EMBODIMENTS FOR CARRYING OUT THE INVENTION

Figure 1:
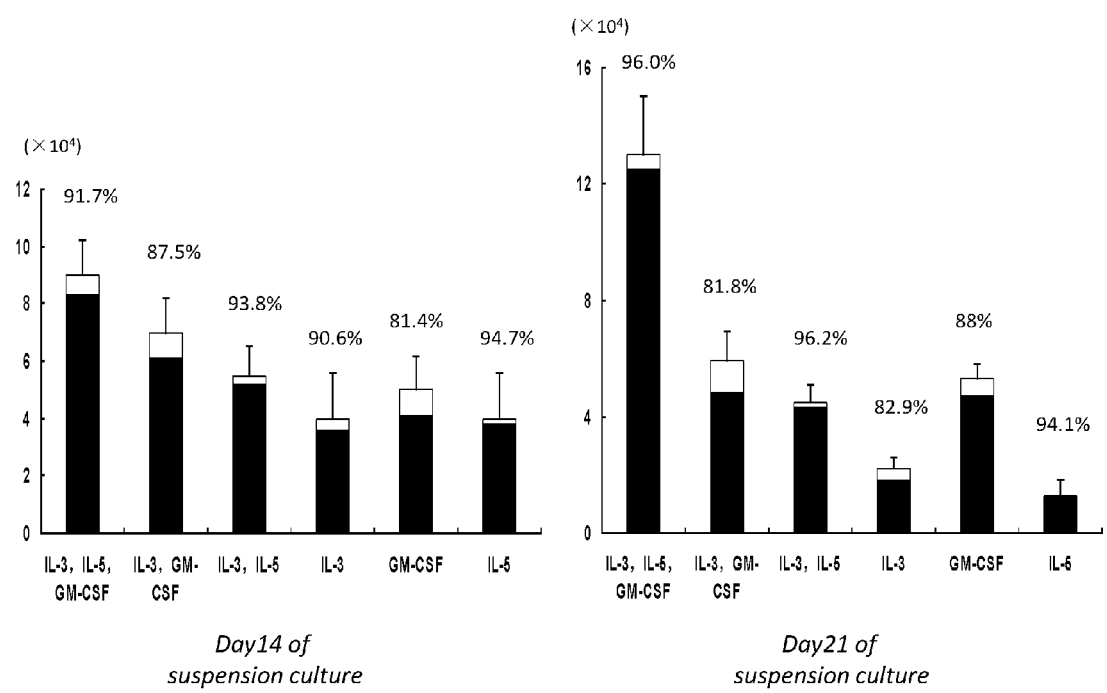
FIG. 1 shows graphs showing the total numbers of cells and the numbers of cells positive for eosinophil peroxidase (EPO) (black) observed after culturing ES cell (H1)-derived CD34-positive cells in media supplemented with combinations of cytokines ((1) human IL-3, human IL-5 and human GM-CSF; (2) human IL-3 and human GM-CSF; (3) human IL-3 and human IL-5; (4) human IL-3; (5) human GM-CSF; (6) human IL-5). The left column shows the results obtained on Day 14 of the culture, and the right column shows the results obtained on Day 21 of the culture. Each number in the figure represents the ratio of EPO-positive cells.

The present invention provides a method for producing human eosinophils by differentiation induction from human pluripotent stem cells using a medium supplemented with an appropriate cytokine(s).

I. Pluripotent Stem Cells

In the present invention, the term "pluripotent stem cells" means cells maintaining their undifferentiated state/pluripotency, which cells are represented by embryonic stem cells (ES cells) and induced pluripotent stem cells (iPS cells). The ES cells may be those produced by nuclear reprogramming of somatic cells. Examples of the pluripotent stem cells other than ES cells include embryonic germ cells (EG cells) derived from primordial germ cells, multipotent germline stem cells (mGS cells) isolated from testis, and multipotent adult progenitor cells (MAPCs) isolated from bone marrow. In the present invention, these pluripotent stem cells are derived from human. In the present invention, the pluripotent stem cells are preferably ES cells or iPS cells.

The method for producing iPS cells is described below.

II. Method for Producing iPS Cells (A) Somatic Cell Source

Somatic cells which may be used as a starting material for preparation of iPS cells may be any cells other than germ cells derived from human, and examples of the somatic cells include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the cells and the age of the human from which the cells are collected are not restricted, and either undifferentiated progenitor cells (including somatic stem cells) or terminally-differentiated mature cells may be used in a similar manner as the source of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

In cases where iPS cells are used as the source of cells to be used for screening for evaluation of drug effectiveness in a patient, it is preferred to collect somatic cells from the patient himself.

The somatic cells separated from human may be precultured, before providing them for the nuclear reprogramming step, in a per se known medium suitable for culture of the cells, depending on the type of the cells. Examples of the medium include, but are not limited to, minimum essential medium (MEM) supplemented with about 5 to 20% fetal bovine serum, Dulbecco's modified Eagle's medium (DMEM), RPMI1640 medium, 199 medium and F12 medium. In cases where a transfection reagent such as cationic liposome is used upon bringing the cells into contact with a nuclear reprogramming substance(s) and an inhibitor of the function of p53 (and, as required, another substance for improvement of the establishment efficiency of iPS cells), the medium may be preferably replaced with a serum-free medium to prevent a decrease in the transfection efficiency.

(B) Nuclear Reprogramming Substances

In the present invention, the "nuclear reprogramming substance(s)" may be a protein factor(s) with which iPS cells can be induced from somatic cells, or a nucleic acid(s) (including those incorporated in a vector) encoding the factor(s). The nuclear reprogramming substance to be used in the present invention may be a gene described in WO 2007/069666. More specific examples of the nuclear reprogramming substance include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmi1, Lin28, Lin28b, Sall1, Sall4, Nanog, Esrrb, Esrrg, Nr5a2, Tbx3 and Glis1. When iPS cells are to be established, these reprogramming substances may be used as a combination, and the combination includes at least 1, 2 or 3, preferably includes 4, of the above reprogramming substances. More specific examples of the combination include the following combinations (only the names of protein factors are described below).

(1) Oct3/4, Klf4, Sox2, and c-Myc (here, Sox2 may be replaced with Sox1, Sox3, Sox15, Sox17 or Sox18. Klf4 may be replaced with Klf1, Klf2 or Klf5. Further, c-Myc may be replaced with L-Myc or N-Myc.)
(2) Oct3/4, Klf4, Sox2, c-Myc, TERT, and SV40 Large T antigen (hereinafter referred to as SV40LT)
(3) Oct3/4, Klf4, Sox2, c-Myc, TERT, and HPV16 E6
(4) Oct3/4, Klf4, Sox2, c-Myc, TERT, and HPV16 E7
(5) Oct3/4, Klf4, Sox2, c-Myc, TERT, HPV6 E6, and HPV16 E7
(6) Oct3/4, Klf4, Sox2, c-Myc, TERT, and Bmi1
(7) Oct3/4, Klf4, Sox2, c-Myc, and Lin28
(8) Oct3/4, Klf4, Sox2, c-Myc, Lin28, and SV40LT
(9) Oct3/4, Klf4, Sox2, c-Myc, Lin28, TERT, and SV40LT
(10) Oct3/4, Klf4, Sox2, c-Myc, and SV40LT
(11) Oct3/4, Esrrb, Sox2, and c-Myc (Esrrb may be replaced with Esrrg.)
(12) Oct3/4, Klf4, and Sox2
(13) Oct3/4, Klf4, Sox2, TERT, and SV40LT
(14) Oct3/4, Klf4, Sox2, TERT, and HPV16 E6
(15) Oct3/4, Klf4, Sox2, TERT, and HPV16 E7
(16) Oct3/4, Klf4, Sox2, TERT, HPV6 E6, and HPV16 E7
(17) Oct3/4, Klf4, Sox2, TERT, and Bmi1
(18) Oct3/4, Klf4, Sox2, and Lin28
(19) Oct3/4, Klf4, Sox2, Lin28, and SV40LT
(20) Oct3/4, Klf4, Sox2, Lin28, TERT, and SV40LT
(21) Oct3/4, Klf4, Sox2, and SV40LT
(22) Oct3/4, Esrrb, and Sox2 (Esrrb may be replaced with Esrrg.)
(23) Oct3/4, Klf4, Sox2, and L-Myc

(24) Oct3/4, Klf4, Sox2, L-Myc, Lin28, and Glis1

In the above list, Lin28b may be used instead of Lin28.

Further, although not included in the above-described (1) to (24), combinations that comprise, in addition to all the constituents in any of these, another arbitrary substance are also included within the scope of the "nuclear reprogramming substances" in the present invention. Further, under conditions where the somatic cells to be subjected to nuclear reprogramming are endogenously expressing a part of the constituents of any of the above (1) to (24) to a level(s) sufficient for nuclear reprogramming, the combination comprising only the other constituents may be included in the scope of the "nuclear reprogramming substances" in the present invention.

Preferred examples of nuclear reprogramming substances, among these combinations, include the combination of 4 factors, Oct3/4, Sox2, Klf4 and c-Myc; and the combination of 3 factors, Oct3/4, Sox2 and Klf4. Further, the combinations of 5 factors and 4 factors in which SV40 Large T antigen is further included are also preferred.

The sequence information for human cDNAs of the above-described nuclear reprogramming substances can be obtained by reference to the NCBI accession numbers described in WO 2007/069666 or WO 2010/098419, and those skilled in the art can easily isolate these cDNAs. The sequence information for human cDNAs of Oct3/4, Sox2, Klf4, c-Myc, Lin28, Lin28b, Esrrb and Esrrg is described as follows: Oct3/4 (NM_002701), Sox2 (NM_003106), Klf4 (NM_004235), c-Myc (NM_002467), Lin28 (NM_024674), Lin28b (NM_001004317), Esrrb (NM_004452) and Esrrg (NM_001438).

In cases where a protein factor itself is used as a nuclear reprogramming substance, the protein factor can be prepared by inserting the obtained cDNA into an appropriate expression vector and introducing the resulting vector to host cells, followed by culturing the resulting cells to obtain a culture and recovering the recombinant protein factor therefrom. On the other hand, in cases where a nucleic acid encoding a protein factor is used as a nuclear reprogramming substance, the obtained cDNA is inserted into a virus vector, plasmid vector, episomal vector or the like to construct an expression vector, and the resulting expression vector is subjected to the nuclear reprogramming step.

(C) Method for Introducing Nuclear Reprogramming Substance to Somatic Cells

In cases where the nuclear reprogramming substance is a protein factor, the substance may be introduced to somatic cells by a per se known method for introduction of a protein to cells. Examples of such a method include methods using a protein transduction reagent, methods using a fusion protein with a transduction domain (PTD) or with a cell-penetrating peptide (CPP), and the microinjection method. Examples of the protein transduction reagent which is commercially available include cationic lipid-based BioPOTER Protein Delivery Reagent (Gene Therapy Systems), Pro-Ject™ Protein Transfection Reagent (PIERCE) and ProVectin (IM-GENEX); lipid-based Profect-1 (Targeting Systems); membrane-permeable-peptide-based Penetratin Peptide (Q biogene) and Chariot Kit (Active Motif); and GenomONE (Ishihara Sangyo Kaisha, Ltd.), which uses the HVJ envelope (inactivated Sendai virus). The introduction may be carried out according to the protocols attached to these reagents, and, in general, it may be carried out as follows. A nuclear reprogramming substance is diluted in an appropriate solvent (e.g., a buffer such as PBS or HEPES), and a transduction reagent is added to the resulting diluent, followed by incubation of the resulting mixture at room temperature for about 5 to 15 minutes to allow formation of a complex. The resultant is then added to the cells after replacement of their medium with a serum-free medium, and incubation is performed at 37° C. for 1 to several hours. Thereafter, the medium is removed and replaced with a serum-containing medium.

Examples of the PTD include those derived from transcellular domains of proteins such as *Drosophila*-derived AntP, HIV-derived TAT (Frankel, A. et al, Cell 55, 1189-93 (1988); Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1 (Morris, M. C. et al. Nature Biotechnol. 19, 1173-6 (2001)), Pep-7 (Gao, C. et al. Bioorg. Med. Chem. 10, 4057-65 (2002)), SynB1 (Rousselle, C. et al. Mol. Pharmacol. 57, 679-86 (2000)), HN-I (Hong, F. D. & Clayman, G L. Cancer Res. 60, 6551-6 (2000)) and HSV-derived VP22. Examples of the CPP derived from PTD include polyarginines such as 11R (Cell Stem Cell, 4:381-384 (2009)) and 9R (Cell Stem Cell, 4:472-476 (2009)).

A fusion protein expression vector in which the cDNA of a nuclear reprogramming substance and a PTD or CPP sequence are incorporated is prepared to cause recombinant expression. The fusion protein is then recovered and used for the introduction. The introduction may be carried out in the same manner as described above except that a protein transduction reagent is not added.

Microinjection is a method wherein a protein solution is placed in a glass needle having a tip diameter of about 1 μm, and the solution is then introduced to a cell by puncture. By this, the protein can be surely introduced into the cell.

The operation of introduction of the protein may be carried out an arbitrary number of times which is not less than 1 (e.g., 1 to 10 times or 1 to 5 times), and the introduction operation may be preferably repeated not less than 2 times (e.g., 3 times or 4 times). In cases where the introduction operation is repeated, it is carried out at intervals of, for example, 6 to 48 hours, preferably 12 to 24 hours.

In cases where the establishment efficiency of iPS cells is important, each nuclear reprogramming substance is preferably used in the form of a nucleic acid encoding it, rather than the protein factor itself. The nucleic acid may be either DNA or RNA, or a DNA/RNA chimera, and the nucleic acid may be either double-stranded or single-stranded. The nucleic acid is preferably double-stranded DNA, especially cDNA.

The cDNA of the nuclear reprogramming substance is inserted into an appropriate expression vector having a promoter which can function in a somatic cell to be used as the host. Examples of the expression vector which may be used include virus vectors such as retroviruses, lentiviruses, adenoviruses, adeno-associated viruses, herpesviruses and Sendai virus; and animal cell expression plasmids (e.g., pA1-11, pXT1, pRc/CMV, pRc/RSV and pcDNAI/Neo).

The type of the vector to be used may be appropriately selected depending on the use of the obtained iPS cells. Examples of the vector which may be used include adenovirus vectors, plasmid vectors, adeno-associated virus vectors, retrovirus vectors, lentivirus vectors, Sendai virus vectors and episomal vectors.

Examples of the promoter to be used in the expression vector include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred.

In addition to the promoter, the expression vector may comprise, as desired, an enhancer, poly (A) addition signal, selection marker gene, SV40 replication origin and/or the like. Examples of the selection marker gene include the dihydrofolate reductase gene, neomycin resistance gene and puromycin resistance gene.

The nucleic acids (nuclear reprogramming genes) as the nuclear reprogramming substances may be separately incorporated into expression vectors, or 2 or more types, preferably 2 to 3 types of the nucleic acids may be incorporated into a single expression vector. In cases where a retrovirus or lentivirus vector, which has high gene transfer efficiency, is used, the former condition is preferably selected, and in cases where a plasmid, adenovirus, episomal vector or the like is used, the latter condition is preferably selected. Further, an expression vector in which 2 or more types of the genes are incorporated and an expression vector in which only one gene is incorporated may be used in combination.

In the above process, in cases where a plurality of reprogramming genes (e.g., 2 or more, preferably 2 or 3, genes selected from Oct3/4, Sox2, Klf4 and c-Myc) are incorporated into a single expression vector, these plurality of genes may be incorporated into the expression vector preferably via a sequence(s) which enable(s) polycistronic expression of the genes. By using the sequence(s) enabling polycistronic expression, the plurality of genes incorporated in the single expression vector can be more efficiently expressed. Preferred examples of the sequences which enable polycistronic expression include the 2A sequence in foot and mouth disease virus (PLoS ONE3, e2532, 2008; Stem Cells 25, 1707, 2007) and the IRES sequence (U.S. Pat. No. 4,937,190 B). The 2A sequence may be preferably used.

The expression vector containing the reprogramming gene(s) may be introduced to the cells by a per se known method selected depending on the type of the vector. For example, in the case of a virus vector, a plasmid containing the nucleic acid is introduced to an appropriate packaging cell (e.g., Plat-E cell) or a complementing cell line (e.g., 293 cell), and the virus vector produced in the culture supernatant is recovered. Cells are then infected with the vector by an appropriate method selected depending on the type of the virus vector. For example, specific methods using a retrovirus vector as the vector are disclosed in WO 2007/69666; Cell, 126, 663-676 (2006); and Cell, 131, 861-872 (2007); and use of a lentivirus vector as the vector is disclosed in Science, 318, 1917-1920 (2007). In cases where iPS cells are used as a cell source for regenerative medicine, expression (reactivation) of the reprogramming gene(s) may increase the risk of carcinogenesis in the tissue regenerated from differentiated cells derived from the iPS cells, so that the reprogramming gene(s) is/are preferably not incorporated into the chromosomes of the cells, and is/are preferably only transiently expressed. From this viewpoint, an adenovirus vector, which is rarely incorporated into the chromosomes, is preferably used. A specific method using an adenovirus vector is disclosed in Science, 322, 945-949 (2008). Further, since adeno-associated viruses also have low frequencies of incorporation into the chromosomes and show less cytotoxicities and less inflammatory actions compared to adenovirus vectors, they can be other examples of preferred vectors. Sendai virus vectors can stably extrachromosomally exist and can be degraded and removed by siRNAs as required, so that they may be similarly preferably used. Examples of the Sendai virus vectors which may be used include those described in J. Biol. Chem., 282, 27383-27391 (2007) and JP 3602058 B.

In cases where a retrovirus vector or a lentivirus vector is used, the introduced gene(s) may be reactivated even after their silencing, so that a method using the Cre/loxP system, in which the nucleic acid(s) encoding the nuclear reprogramming substance(s) is/are excised when the nucleic acid(s) became unnecessary, is preferably used. That is, the loxP sequences are arranged in the both ends of the nucleic acid(s), and, after induction of iPS cells, Cre recombinase is allowed to act on the cells using a plasmid vector or an adenovirus vector, thereby enabling excision of the region between the loxP sequences. Further, since the enhancer-promoter sequence in the LTR U3 region may upregulate a host gene in its vicinity by insertional mutagenesis, it is preferred to use a 3'-self-inactivating (SIN) LTR wherein the sequence is deleted or substituted by a polyadenylation sequence of SV40 or the like, in order to avoid regulation of expression of an endogenous gene by the LTR outside the loxP sequences which has not been excised and is remaining in the genome. A specific method using the Cre-loxP system and an SIN LTR is disclosed in Chang et al., Stem Cells, 27: 1042-1049 (2009).

On the other hand, in cases where the vector is a plasmid vector, which is a nonviral vector, the vector may be introduced to the cells by using the lipofection method, liposome method, electroporation method, calcium phosphate coprecipitation method, DEAE-dextran method, microinjection method, gene gun method or the like. Specific examples of the method using a plasmid as the vector include those described in Science, 322, 949-953 (2008) and the like.

In cases where a plasmid vector, adenovirus vector or the like is used, the gene transfer may be carried out an arbitrary number of times which is not less than 1 (e.g., 1 to 10 times or 1 to 5 times). In cases where not less than 2 types of expression vectors are introduced to somatic cells, all of these types of vectors are preferably introduced to the somatic cells at the same time, and also in such cases, the operation of the gene transfer may be carried out an arbitrary number of times which is not less than 1 (e.g., 1 to 10 times or 1 to 5 times). The operation of gene transfer may be preferably repeated not less than 2 times (e.g., 3 times or 4 times).

Also in cases where an adenovirus or a plasmid is used, the transgene(s) may be incorporated into a chromosome(s). Therefore, it is eventually necessary to confirm, by Southern blotting and/or PCR, that the gene(s) is/are not inserted in a chromosome(s). Therefore, it may be advantageous to use a method to remove the transgene(s) after its incorporation into a chromosome(s), such as the above-described Cre-loxP system. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect. Specific methods using the piggyBac transposon are disclosed in Kaji, K. et al., Nature, 458: 771-775 (2009) and Woltjen et al., Nature, 458: 766-770 (2009).

Another preferred non-incorporation type vector is an episomal vector, which can be extrachromosomally and autonomously replicated. A specific method using an episomal vector is disclosed in Yu et al., Science, 324, 797-801 (2009). In one especially preferred mode of the present invention, an expression vector is constructed by inserting a reprogramming gene(s) into an episomal vector wherein loxP sequences are arranged in the same direction in the 5'-side and the 3'-side of the vector elements required for replication of the episomal vector. After introduction of the resulting vector to somatic cells, the vector, existing as an episome, drops from the iPS cells at an early stage without occurrence of even transient incorporation of the exogenous nucleic acid factors constituting the vector (including the reprogramming gene(s)) into the genome of the cells.

Examples of the episomal vector to be used in the present invention include those having, as vector elements, sequences necessary for their autonomous replication, which are derived from EBV, SV40 and/or the like. More specifically, the vector elements necessary for autonomous replication are a replication origin and a gene encoding a protein that is bound to the replication origin to regulate replication, and examples thereof include the replication origin oriP and the EBNA-1 gene in the case of EBV; and the replication origin ori and the SV40 large T antigen gene in the case of SV40.

Further, the episomal expression vector contains a promoter that regulates transcription of the reprogramming gene. Examples of the promoter which may be used include those described above. The episomal expression vector may further contain, as desired, an enhancer, poly (A) addition signal, selection marker gene and/or the like, as described above. Examples of the selection marker gene include the dihydrofolate reductase gene and the neomycin resistance gene.

The episomal vector may be introduced to cells by using the lipofection method, liposome method, electroporation method, calcium phosphate coprecipitation method, DEAE-dextran method, microinjection method, gene gun method or the like. Specific examples of the method include those described in Science, 324, 797-801 (2009) and the like.

Confirmation of whether or not the vector elements necessary for replication of the reprogramming gene(s) were removed from the iPS cells may be carried out by Southern blot analysis or PCR analysis using, as a probe or a primer, a nucleic acid containing a nucleotide sequence inside the vector elements and/or a nucleotide sequence in the vicinity of the loxP sequence, and, as a template, the episome fraction isolated from the iPS cells, followed by investigation of the presence or absence of a band or the length at which a band is detected. Preparation of the episome fraction may be carried out by a method well-known in the art, and examples of the method include those described in Science, 324: 797-801 (2009) and the like.

(D) Inhibitor of Function of p53

In the present invention, it can be expected that the establishment efficiency of iPS cells can be further increased by bringing, in addition to the nuclear reprogramming substance(s) described above, an inhibitor(s) of the function of p53 into contact with the cells. Examples of the inhibitor of the function of p53 include, but are not limited to, the chemical inhibitor of p53 described in WO 2009/157593; dominant-negative mutants of p53 and nucleic acids encoding them; anti-p53 antagonistic antibodies and nucleic acids encoding them; decoy nucleic acids containing the consensus sequences of p53-response elements; and inhibitors of the p53 pathway.

(E) Substance for Improvement of Establishment Efficiency of iPS Cells

It is expected that the establishment efficiency of iPS cells can be further increased by bringing, in addition to the reprogramming factor(s) and the like described above, another/ other known substance(s) for improvement of the establishment efficiency of iPS cells into contact with the somatic cells. Examples of such substances for improvement of the establishment efficiency of iPS cells include, but are not limited to, histone deacetylase (HDAC) inhibitors [e.g., low molecular inhibitors such as valproic acid (VPA) (Nat. Biotechnol., 26(7): 795-797 (2008)), trichostatin A, sodium butyrate, MC 1293 and M344; and nucleic acid-based expression inhibitors such as siRNAs and shRNAs against HDAC (e.g., HDAC1 siRNA Smartpool (Millipore) and HuSH 29mer shRNA Constructs against HDAC1 (OriGene))]; G9a histone methyltransferase inhibitors [e.g., low molecular inhibitors such as BIX-01294 (Cell Stem Cell, 2: 525-528 (2008)); and nucleic acid-based expression inhibitors such as siRNAs and shRNAs against G9a (e.g., G9a siRNA (human) (Santa Cruz Biotechnology))]; L-calcium channel agonists (e.g., Bayk8644) (Cell Stem Cell, 3, 568-574 (2008)); UTF1 (Cell Stem Cell, 3, 475-479 (2008)); Wnt Signaling (e.g., soluble Wnt3a) (Cell Stem Cell, 3, 132-135 (2008)); 2i/LIF (2i is an inhibitor of mitogen-activated protein kinase signaling and glycogen synthase kinase-3, PLoS Biology, 6(10), 2237-2247 (2008)); and ES cell-specific miRNAs [e.g., miR-302-367 cluster (Mol. Cell. Biol. doi:10.1128/MCB.00398-08 and WO 2009/075119), miR-302 (RNA (2008) 14: 1-10), and miR-291-3p, miR-294 and miR-295 (these are described in Nat. Biotechnol. 27: 459-461 (2009))]. In the above examples, each nucleic acid-based expression inhibitor may also be in the form of an expression vector containing DNA encoding an siRNAs or shRNA.

Among the constituents of the nuclear reprogramming substance(s), SV40 large T and the like may be included within the scope of the substances for improvement of the establishment efficiency of iPS cells in view of the fact that they are not indispensable for nuclear reprogramming of somatic cells and are therefore auxiliary factors. Currently, the mechanism of nuclear reprogramming is unknown, so that auxiliary factors which are not indispensable for nuclear reprogramming may be positioned, for convenience, either as nuclear reprogramming factors or substances for improvement of the establishment efficiency of iPS cells. That is, the process of nuclear reprogramming of somatic cells can be understood, in its entirety, as a phenomenon caused by contacting of the nuclear reprogramming substance(s) and the substance(s) for improvement of the establishment efficiency of iPS cells with somatic cells, so that it is not necessary for those skilled in the art to distinguish between these substances.

(F) Improvement of Establishment Efficiency by Culture Conditions

In the process of nuclear reprogramming of somatic cells, the establishment efficiency of iPS cells can be further improved by culturing the cells under hypoxic conditions. In the present description, the term "hypoxic conditions" means that the oxygen concentration in the atmosphere during the culture of cells is significantly lower than that in the air. Specific examples of the conditions include those wherein the oxygen concentration is lower than the oxygen concentration in the atmosphere commonly used in cell culture, that is, 5 to 10% $CO_2$/95 to 90% air, and, for example, conditions wherein the oxygen concentration in the atmosphere is not more than 18% are included in such examples. The oxygen concentration in the atmosphere is preferably not more than 15% (e.g., not more than 14%, not more than 13%, not more than 12% or not more than 11%), not more than 10% (e.g., not more than 9%, not more than 8%, not more than 7% or not more than 6%), or not more than 5% (e.g., not more than 4%, not more than 3% or not more than 2%). Further, the oxygen concentration in the atmosphere is preferably not less than 0.1%

(e.g., not less than 0.2%, not less than 0.3% or not less than 0.4%), not less than 0.5% (e.g., not less than 0.6%, not less than 0.7%, not less than 0.8% or not less than 0.95), or not less than 1% (e.g., not less than 1.1%, not less than 1.2%, not less than 1.3% or not less than 1.4%).

The method for creating a hypoxic state in the cellular environment is not restricted, and the simplest and preferred examples thereof include a method wherein the cells are cultured in a $CO_2$ incubator with which the oxygen concentration can be controlled. The $CO_2$ incubator with which the oxygen concentration can be controlled is commercially available from various equipment manufacturers (for example, $CO_2$ incubators for hypoxic culture produced by manufacturers such as Thermo scientific, Ikemoto Scientific Technology Co., Ltd., Juji Field Inc. and Wakenyaku Co., Ltd. may be used).

The timing to start cell culture under hypoxic conditions is not restricted as long as the establishment efficiency of iPS cells, relative to the establishment efficiency at the normal oxygen concentration (20%), is improved, and may be before the contact, at the same time as the contact, or after the contact, of somatic cells with the nuclear reprogramming substance(s). For example, the culture under hypoxic conditions is preferably carried out immediately after the contact of somatic cells with the nuclear reprogramming substance(s), or after a certain period (for example, 1 to 10 (e.g., 2, 3, 4, 5, 6, 7, 8 or 9) days) following the contact.

The period of culture of the cells under hypoxic conditions is also not restricted as long as the establishment efficiency of iPS cells, relative to the establishment efficiency at the normal oxygen concentration (20%), is improved, and examples of the period include, but are not limited to, not less than 3 days, not less than 5 days, not less than 7 days or not less than 10 days, and not more than 50 days, not more than 40 days, not more than 35 days or not more than 30 days. The preferred culture period under hypoxic conditions varies depending on the oxygen concentration in the atmosphere, and those skilled in the art can appropriately control the culture period depending on the oxygen concentration to be used. Further, in an embodiment wherein candidate colonies of iPS cells are selected using drug resistance as an index, the conditions are preferably changed again from hypoxic conditions to normal oxygen concentration conditions before starting selection using a drug.

Further, the preferred timing to start cell culture under hypoxic conditions and the preferred culture period may vary depending on, for example, the type(s) of the nuclear reprogramming substance(s) employed and the establishment efficiency of iPS cells under conditions wherein the oxygen concentration is normal.

III. Method for Inducing Differentiation of Pluripotent Stem Cells into Eosinophils The method of the present invention for inducing differentiation of pluripotent stem cells into eosinophils comprises the 4 steps below.
(1) co-culturing, in the presence of VEGF, human pluripotent stem cells with cells separated from the AGM region of a mammalian fetus;
(2) performing suspension culture of the cells obtained in Step (1) using a medium comprising IL-3, IL-6, Flt3 ligand, SCF, TPO and serum;
(3) performing suspension culture of the cells obtained in Step (2) using a medium comprising IL-3, SCF, GM-CSF and serum; and, optionally,
(4) performing suspension culture of the cells obtained in Step (3) using a medium comprising IL-3, IL-5 and serum.

Here, the term "AGM (aorta, gonad and mesonephros) region" means the portion in a fetus surrounded by the dorsal aorta, gonad and mesonephros, which is preferably the portion in a mouse fetus of 10.5 days. The cells separated from the AGM region are preferably treated with γ-ray for removal of hematopoietic cells. Specific examples of the cells separated from the AGM region include cells established by the method described in JP 2001-37471 A, which are positive for VECAM-1, CD13 and Sca-1 and produce IL-6 and oncostatin M. The cells are especially preferably AGM-S3 described in JP 2001-37471. During the co-culture, the cells separated from the AGM region are preferably present in excess with respect to the human pluripotent stem cells. Further, the cells separated from the AGM region are preferably subjected to radiation processing or mitomycin C treatment to impair their growth function before the co-culture.

The term "suspension culture" means culturing of cells using a non-adherent type culture dish.

The Flt3 ligand is a cytokine which can be specified by the nucleic acid sequence information shown as NM_001459, whose receptor is a transmembrane-type tyrosine kinase, flt3.

The cytokines to be used in the present invention, such as VEGF, IL-3, IL-5, IL-6, Flt 3 ligand, SCF, TPO and GM-CSF, may be either naturally-occurring cytokines or recombinant cytokines prepared by genetic engineering. Each of these does not need to contain its entire length, and may be a partial protein or peptide containing the region involved in its binding to a receptor. Further, the cytokine may be a protein or peptide whose amino acid sequence and/or spatial structure is/are modified to an extent at which the binding capacity to the receptor is not impaired. Further, the cytokine may be a protein, peptide or agent which can function as an agonist to the receptor of the cytokine.

The concentration of each cytokine is not restricted as long as the cells of interest can be obtained therewith, and may be 5 ng/ml to 50 ng/ml, preferably 10 ng/ml to 20 ng/ml in the case of VEGF; 5 ng/ml to 50 ng/ml, preferably 10 ng/ml in the case of IL-3; 5 ng/ml to 50 ng/ml, preferably 10 ng/ml in the case of IL-5; 50 ng/ml to 200 ng/ml, preferably 100 ng/ml in the case of IL-6; 5 ng/ml to 50 ng/ml, preferably 10 ng/ml in the case of Flt3 ligand; 50 ng/ml to 200 ng/ml, preferably 100 ng/ml in the case of SCF; 5 ng/ml to 50 ng/ml, preferably 10 ng/ml in the case of TPO; and 5 ng/ml to 50 ng/ml, preferably 10 ng/ml in the case of GM-CSF.

The concentration of the serum may be 5% to 20%, preferably 10%.

The medium to be used in the step of differentiation induction may be any medium for culturing mammalian cells, and examples of the medium include Iscove's modified Dulbecco's medium (IMDM), minimum essential medium (MEM), Dulbecco's modified Eagle's medium (DMEM), RPMI1640 medium, 199 medium and F12 medium. The medium is preferably IMDM. The medium may additionally contain one or more serum replacements such as albumin, transferrin, sodium selenite, Knockout Serum Replacement (KSR) (serum replacement for FBS in ES cell culture), N2 supplement (Invitrogen), B27 supplement (Invitrogen), fatty acids, insulin, collagen precursors, trace elements, 2-mercaptoethanol and/or 3'-thiolglycerol; and may further contain one or more substances such as lipids, amino acids, L-glutamic acid, Glutamax, non-essential amino acids, vitamins, antibiotics, antioxidants, pyruvic acid, buffers and/or inorganic salts.

In Step (1), for reducing the stress at an early stage of the culture, the human pluripotent stem cells and the cells separated from the AGM region of a mammalian fetus may be cultured for 1 to 5 days, preferably for 3 days, in a VEGF-free medium for pluripotent stem cells. Examples of the medium for pluripotent stem cells include those containing (1) DMEM, DMEM/F12 or DME medium supplemented with 10 to 15% FBS (these media may further contain leukemia inhibitory factor (LIF), penicillin/streptomycin, puromycin, L-glutamine, non-essential amino acids, β-mercaptoethanol and/or the like, as appropriate), which is a medium described in H. Suemori et al. (2006), Biochem. Biophys. Res. Commun., 345:926-932; (2) a medium for ES cell culture containing bFGF or SCF, such as a medium for culturing mouse ES cells (e.g., TX-WES medium, Thromb-X) or a medium for culturing primate ES cells (e.g., medium for primate (human and monkey) ES cells (ReproCELL), mTeSR-1); or the like.

The eosinophil in the present invention is a cell containing in its granule the major basic protein (MBP), eosinophil cationic protein (ECP), eosinophil peroxidase (EPO) and eosinophil-derived neurotoxin (EDN), and is preferably a cell having a capacity to release EDN in response to stimulation by secretory immunoglobulin A (sIgA) and a capacity to migrate in response to stimulation by IL-5, Eotaxin and fMLP.

In terms of the period of each step, the step of "(1) co-culturing, in the presence of VEGF, human pluripotent stem cells with cells separated from the AGM region of a mammalian fetus" is carried out for not less than 10 days, preferably for 10 to 18 days, more preferably for 14 days. The step of "(2) performing suspension culture using a medium comprising IL-3, IL-6, Flt3 ligand, SCF, TPO and serum" is carried out for not less than 4 days, preferably for 5 to 10 days, more preferably for 7 days. The step of "(3) performing suspension culture using a medium comprising IL-3, SCF, GM-CSF and serum" is carried out for not less than 4 days, preferably for 5 to 10 days, more preferably for 7 days. The step of "(4) performing suspension culture using a medium comprising IL-3, IL-5 and serum" is carried out for not less than 4 days, preferably for 5 to 10 days, more preferably for 7 days.

IV. A Screening Method
Method for Screening Effective Component

The present invention provides a screening method wherein eosinophils obtained as described above are brought into contact with test substances in order to screen a substance which reduces the migratory capacity of the eosinophils.

The test substance in the present invention may be any known or novel compound, and examples of the test substance include nucleic acids; carbohydrates; lipids; proteins; peptides; organic low molecular weight compounds; compound libraries prepared using the combinatorial chemistry technology; random peptide libraries prepared by solid phase synthesis or the phage display method; and natural components derived from microorganisms, animals, plants, marine organisms and the like.

The screening method is a method wherein a detection value obtained when eosinophils are not brought into contact with a test substance is compared with a detection value obtained when eosinophils are brought into contact with the test substance, and a substance that shows a lower detection value upon the contact is selected as an effective component.

The detection of the migratory capacity of eosinophils herein may be carried out by, for example, using transwell (Corning).

The thus screened test substance can be used as a therapeutic agent for bronchial asthma, allergic disease and/or atopic dermatitis.

Method for Screening Tailor-Made Drug

In the present invention, the term "tailor-made drug" means a therapeutic agent most suitable for each individual patient, who has unique characteristics.

The present invention provides a method for screening a therapeutic agent that reduces the migratory capacity of eosinophils, wherein the eosinophils obtained by differentiation induction of induced pluripotent stem cells produced from somatic cells of a subject suffering from bronchial asthma, allergic disease and/or atopic dermatitis are brought into contact with known therapeutic agents. The thus screened therapeutic agent can be an optimal therapeutic agent for the subject from whom the induced pluripotent stem cells were established.

Examples of the known therapeutic agent in the present invention include, but are not limited to, chemical mediator release inhibitors (e.g., sodium cromoglycate (Intal), tranilast (Rizaben), amlexanox (Solfa) and pemirolast potassium (Alegysal)); chemical mediator receptor antagonists (e.g., (1) antihistaminic agents such as d-chlorpheniramine maleate (Polaramine), clemastine fumarate (Tavegyl), ketotifen fumarate (Zaditen), azelastine hydrochloride (Azeptin), oxatomide (Celtect), mequitazine (Zesulan, Nipolazine), emedastine fumarate (Daren, Remicut), cetirizine hydrochloride (Zyrtec), Levocabastine hydrochloride (Livostin), fexofenadine hydrochloride (Allegra) and olopatadine hydrochloride (Allelock), (2) thromboxane A2 antagonists such as Ramatroban (Baynas), (3) leukotriene antagonists such as pranlukast hydrate (Onon)); Th2 cytokine inhibitors (e.g., suplatast tosylate (IPD)); steroid drugs (e.g., (1) topical steroid agents such as beclomethasone dipropionate (Beconase, Aldecin, Rhinocort), flunisolide (Synaclyn) and fluticasone propionate (Flunase), (2) oral steroid drugs such as Celestamine (chlorpheniramine maleate-containing drug); autonomic drugs (e.g., (1) α stimulators such as naphazoline nitrate (Privina), tetrahydrozoline nitrate (Narbel), oxymetazoline hydrochloride (Nasivin) and tramazoline hydrochloride (Towk), (2) anticholinergic drugs such as ipratropium bromide (Atrovent) and flutropium bromide (Flubron)); and biologics (e.g., Neurotropin, Asthremedin and MS antigen)). The therapeutic agent may also be one which will be developed in the future and available at the time point at which the screening is to be carried out.

The present invention will now be described in more detail by way of Examples, but, needless to say, the present invention is not restricted to these.

EXAMPLES

Cells

AGM-S3 cells and iPS cells (253G1) were established and cultured by the conventional method described below (JP 2001-37471 A and Nakagawa M, et al., Nat Biotechnol 26 (1), 101, 2008). Briefly, the AGMS-3 cells were established by excising the AGM region from a mouse fetus and subjecting the region to γ-ray irradiation to remove hematopoietic cells, followed by cloning by the limiting dilution method. The AGMS-3 has been confirmed to have an activity to support the growth of human haematopoietic stem cells.

As ES cells, the H1 strain described in Thomson J A, et al, Science. 282:1145-7 (1998) was used. As iPS cells, 201B6 and 201B7 described in Takahashi K, et al, Cell. 131:861-72 (2007) and 253G1 and 253G4 described in Nakagawa M, et al, Nat Biotechnol. 26:101-6253 (2008) were used. H1 is also available from WiCell Research Institute, and 201B6, 201B7, 253G1 and 253G4 are also available from RIKEN CELL BANK.

Study on Method for Differentiation Induction into Eosinophils

On AGMS-3 cells preliminarily cultured and treated with radiation (15-18 Gy), picked colonies of ES cells (H1) were placed, and the colonies were cultured in a maintenance medium for ES cells or iPS cells (Primate ES medium supplemented with 10 μg/ml bFGF (ReproCELL)) for 3 days. Subsequently, the medium was replaced with IMDM (Gibco) supplemented with 10% FBS (Hyclone), non-essential amino acid solution (Gibco), transferrin (Sigma), 2-mercaptoethanol (Wako), glutamine (Gibco), ascorbic acid (Sigma) and 20 ng/ml rhVEGF (Wako), and the culture was continued for 11 days. The cells were detached from the plate using 0.25% trypsin/EDTA solution (Gibco), and subjected to suspension culture using, as a medium, IMDM supplemented with 10% FBS, 100 ng/ml human SCF (Wako), 10 ng/ml human IL-3, 100 ng/ml human IL-6, 10 ng/ml human Flt3-ligand (R&D Systems) and 10 ng/ml human thrombopoietin (TPO) for 7 days on a non-adherent dish (Sumilon). By FACS, $5\times10^3$ CD34-positive cells obtained by the culture were isolated, and combinations of cytokines ((1) human IL-3, human IL-5 and human GM-CSF; (2) human IL-3 and human GM-CSF; (3) human IL-3 and human IL-5; (4) human IL-3; (5) human GM-CSF; (6) human IL-5) were added to the medium, followed by performing suspension culture for 14 days or 21 days. As a result of measurement of the cell number and the positive rate of eosinophil peroxidase (EPO), the cell number was large in the case where (1) human IL-3, human IL-5 and human GM-CSF were used, and the EPO positive rate was high in the case where (3) human IL-3 and human IL-5 were used (FIG. 1). From the above study, the following method for induction of eosinophils was established.

Method for Differentiation Induction into Eosinophils

Step 1

On AGMS-3 cells preliminarily cultured and treated with radiation (15-18 Gy), picked colonies of ES cells (H1) or iPS cells (201B6, 201B7, 253G1 or 253G4) were placed, and the colonies were cultured in a maintenance medium for ES cells or iPS cells for 3 days. Subsequently, the medium was replaced with IMDM (Gibco) supplemented with 10% FBS (Hyclone), non-essential amino acid solution (Gibco), transferrin (Sigma), 2-mercaptoethanol (Wako), glutamine (Gibco), ascorbic acid (Sigma) and 20 ng/ml rhVEGF (Wako), and the culture was continued for 11 days.

Step 2

The cells established in Step 1 were detached from the plate using 0.25% trypsin/EDTA solution (Gibco), and subjected to suspension culture using, as a medium, IMDM supplemented with 10% FBS, 100 ng/ml human SCF (Wako), 10 ng/ml human IL-3, 100 ng/ml human IL-6, 10 ng/ml human Flt3-ligand (R&D Systems) and 10 ng/ml human thrombopoietin (TPO) for 7 days on a non-adherent dish (SUMILON).

Step 3

The medium was replaced with IMDM medium supplemented with 10% FBS, 100 ng/ml SCF, 10 ng/ml human IL-3 and 10 ng/ml human GM-CSF, and suspension culture was performed for 7 days.

Step 4

The medium was replaced with IMDM medium supplemented with 10% FBS, 10 ng/ml human IL-3 and 10 ng/ml human IL-5, and suspension culture was performed for 7 days.

Measurement of Amount of EDN Released (Evaluation of Eosinophils)

Figure 2:
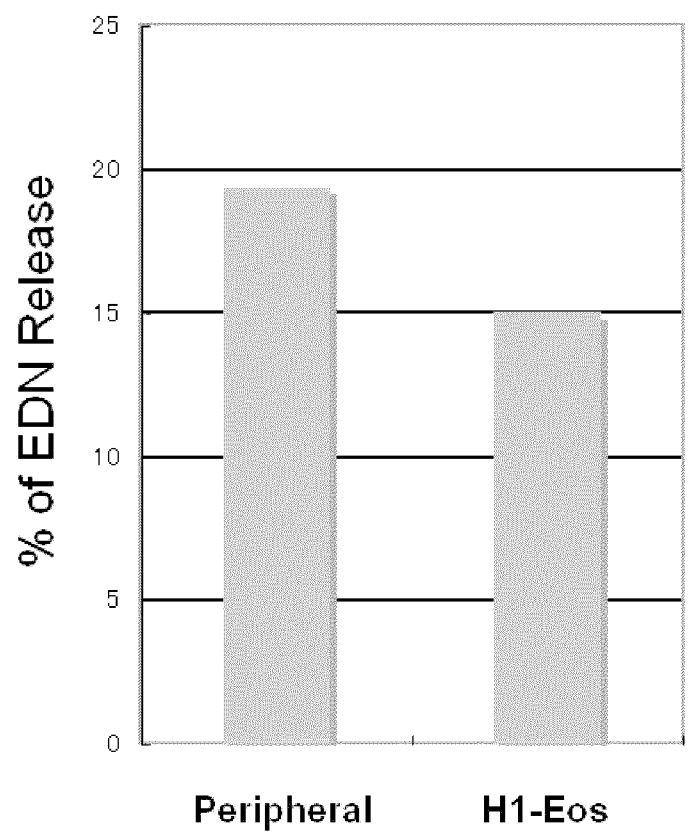
FIG. 2 shows the EDN-releasing abilities of peripheral blood-derived eosinophils and ES cell (H1)-derived eosinophils.

Eosinophils (H1-Eos) established by the method described above were cultured in a dish preliminarily coated with 1 or 100 μg/ml secretory immunoglobulin A (sIgA) (ICN Biomedicals) per 400 μl, and the EDN level in the medium was measured with EDN-ELISA kit (R&D). As a result of comparison of the amount of released EDN with that of peripheral blood-derived eosinophils (FIG. 2), the ES cell (H1)-derived eosinophils were found to show a slightly smaller amount of EDN released, but, compared to the eosinophils obtained without performing Step 4, the amount of released EDN in the case where Step 4 was carried out was closer to that of the peripheral blood-derived eosinophils.

Measurement of Migratory Capacity (Evaluation of Eosinophils)

Figure 3:
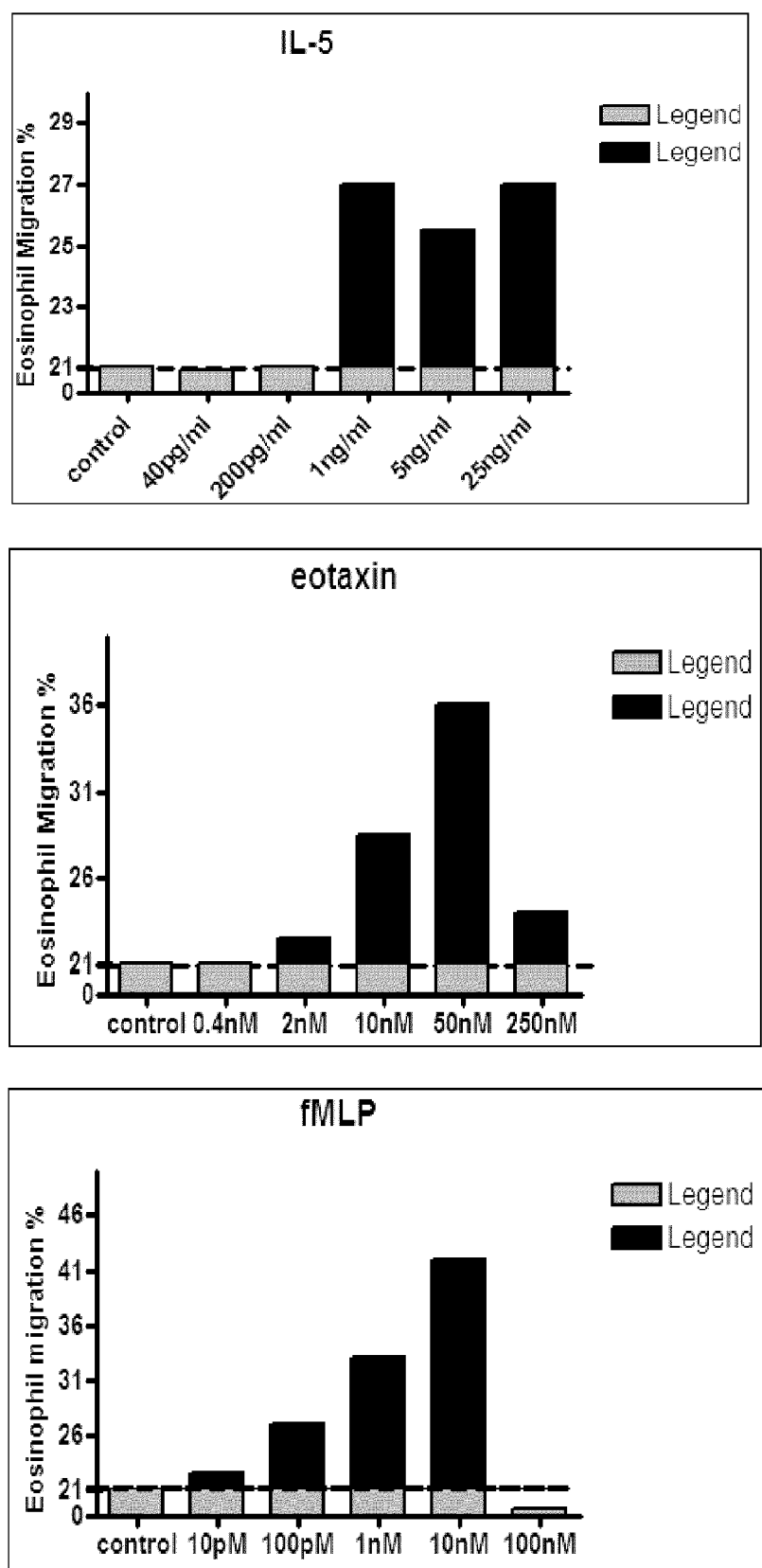
FIG. 3 shows the migratory capacities of ES cell (H1)-derived eosinophils observed after addition of IL-5 (top panel), Eotaxin (middle panel) or fMLP (bottom panel) at various concentrations.

Eosinophils established from ES cells (H1) by the above method were transferred to Transwell, and 1640 medium supplemented with 5% FBS was added thereto. IL-5 (0.2 ng/ml to 25 ng/ml), Eotaxin (0.4 nM to 250 nM) and fMLP (10 pM to 100 nM) at various concentrations were added thereto, and culture was performed for 1 to 2 hours. Thereafter, the number of cells migrated from the top layer to the bottom layer was measured (FIG. 3). As a result, it was confirmed that the ES cell-derived eosinophils migrate in response to the respective types of stimulation, and hence that these cells have a mature function.

iPS Cell-Derived Eosinophils

Figure 4:
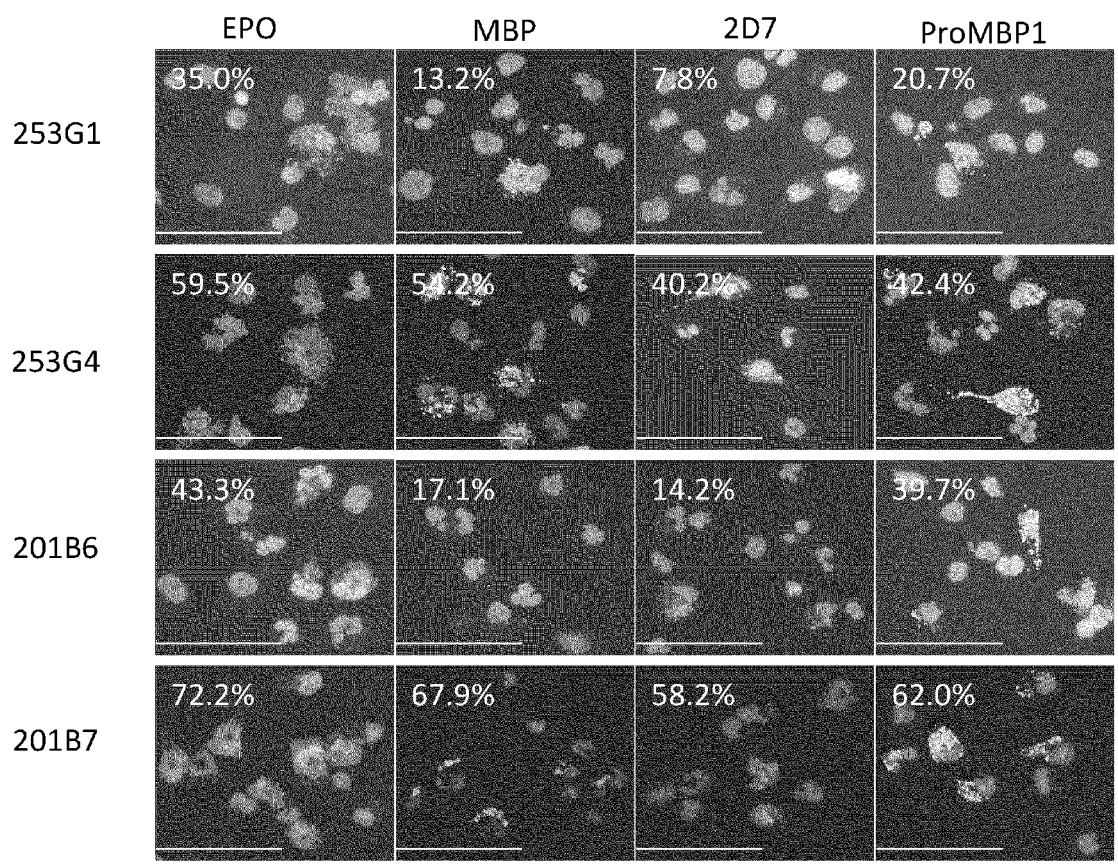
FIG. 4 shows micrographs showing images of iPS cell (253G1, 253G4, 201B6 or 201B7)-derived eosinophils stained with EPO, MBP, 2D7 or ProMBP1. Each number in the figure represents the ratio of cells positive for each marker.

Differentiation induction was carried out using iPS cells (201B6, 201B7, 253G1 or 253G4) until Step 3, and the numbers of cells positive for EPO, MBP, 2D7 and ProMBP1 were measured (FIG. 4). As a result, mature eosinophils, which are positive for EPO and MBP and negative for 2D7 and ProMBP1, were observed.

INDUSTRIAL APPLICABILITY

By using the present invention, human eosinophils can be efficiently produced from human pluripotent stem cells. Therefore, the present invention is very useful as a method for screening a therapeutic agent for allergic diseases using eosinophils, and also very useful for selection of the so-called tailor-made drug wherein eosinophils established from each individual patient are used to select a therapeutic drug most suitable for the individual.

What is claimed is:

1. A method for producing human eosinophils from human induced pluripotent stem cells, said method comprising the steps of:
   (1) co-culturing, in the presence of vascular endothelial growth factor (VEGF), human induced pluripotent stem cells with stromal cells separated from the aorta gonad and mesonephros (AGM) region of a mammalian fetus;
   (2) performing suspension culture of the cells obtained in Step (1) using a medium comprising IL-3, IL-6, Fms-related tyrosine kinase 3 (Flt3) ligand, stem cell factor (SCF), thrombopoietin (TPO) and serum;
   (3) performing suspension culture of the cells obtained in Step (2) using a medium comprising IL-3, SCF, Granulocyte Macrophage colony-stimulating factor (GM-CSF) and serum; and, optionally,
   (4) performing suspension culture of the cells obtained in Step (3) using a medium comprising IL-3, IL-5 and serum.

2. The method according to claim 1, wherein said cells separated from the AGM region of a mammalian fetus are AGMS-3.

3. The method according to claim 1, wherein each of Step (2), Step (3) and Step (4) is carried out for 7 days.

4. The method according to claim 1, wherein the concentration of serum is 10% in Step (2), Step (3) and Step (4).

5. The method according to claim 1, wherein the produced human eosinophils are eosinophils that migrate in response to stimulation by at least one cytokine selected from the group consisting of IL-5, Eotaxin and Formyl-Methionyl-Leucyl-Phenylalanine (fMLP).

6. A method for screening a therapeutic agent for bronchial asthma, allergic disease and/or atopic dermatitis, said method comprising the steps of:

produce human eosinophils from human induced pluripotent stem cells by the method according to claim 1, and bringing the obtained human eosinophils into contact with test substances to select a test substance that reduces the migratory capacity of said eosinophils, wherein the selected test substance is considered a therapeutic agent.

7. The screening method according to claim 6, wherein said human induced pluripotent stem cells are induced pluripotent stem cells produced from somatic cells of a subject suffering from bronchial asthma, allergic disease and/or atopic dermatitis.

* * * * *